United States Patent
Ito et al.

(10) Patent No.: US 6,770,667 B1
(45) Date of Patent: Aug. 3, 2004

(54) AMIDE COMPOUNDS

(75) Inventors: Kiyotaka Ito, Osaka (JP); Glen W. Spears, Osaka (JP); Fumie Takahashi, Osaka (JP); Akira Yamada, Osaka (JP); Masaki Tomishima, Osaka (JP); Hiroshi Miyake, Osaka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 10/088,088

(22) PCT Filed: Sep. 26, 2000

(86) PCT No.: PCT/JP00/06623

§ 371 (c)(1),
(2), (4) Date: Mar. 21, 2002

(87) PCT Pub. No.: WO01/25229

PCT Pub. Date: Apr. 12, 2001

(30) Foreign Application Priority Data

Oct. 1, 1999 (AT) .............................................. PQ3198

(51) Int. Cl.[7] .................... C07D 233/64; A61K 31/4164
(52) U.S. Cl. ................. 514/397; 548/312.1; 548/314.7; 548/315.1; 548/338.1; 514/399
(58) Field of Search ........................... 548/312.1, 314.7, 548/315.1, 338.1; 514/397, 399

(56) References Cited

U.S. PATENT DOCUMENTS

| 4,301,169 A | 11/1981 | Yamanaka | .................. 424/273 |
| 5,077,409 A | 12/1991 | Wissner | ...................... 546/121 |

FOREIGN PATENT DOCUMENTS

WO        96 23783        8/1996

*Primary Examiner*—Mukund J. Shah
*Assistant Examiner*—Kahsay Habte
(74) *Attorney, Agent, or Firm*—Oblon, Spivak, McClelland, Maier & Neustadt, P.C.

(57) ABSTRACT

The present invention is a compound and pharmaceutical composition comprising a compound of formula (I):

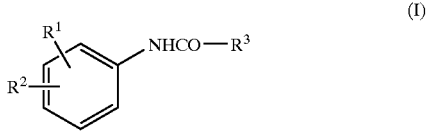

wherein $R^1$ is a 4-(lower) alkyl-imidazol-1-yl or a 4,5-di (lower) alkyl-imidazol-1-yl group, $R^2$ is a hydrogen atom or a lower alkyl group, and $R^3$ is a fluorenyl group. The compound of formula (I) includes pharmaceutically acceptable salts: The compound of formula (I) and salts thereof have 5-HT antagonism activity.

14 Claims, No Drawings

AMIDE COMPOUNDS

TECHNICAL FIELD

The present invention relates to novel amide compounds and salts thereof. More particularly, it relates to novel amide compounds and salts thereof which have pharmacological activities such as 5-hydroxytryptarine (5-HT) antagonism and the like.

Said amide compounds and their salts are useful as a 5HT antagonist for treating or preventing central nervous system (CNS) disorders such as anxiety, depression, obsessive compulsive disorders, migraine,.anorexia, Alzheimer's disease, sleep disorders, bulimia, panic attacks, withdrawal from drug abuse (e.g., with cocaine, ethanol, nicotine and benzodiazepines), schizophrenia, and also disorders associated with spinal trauma and/or head injury such as hydrocephalus in human being and animals.

BACKGROUND ART

With regard to the state of the art in this field, for example, the following amide compounds are disclosed in Japanese Patent Kokai No. Hei 11(1999)-130750.

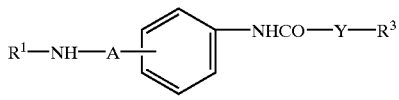

wherein $R^1$ is quinolyl, quinazolinyl, isoquinolyl or pyridyl group, $R^3$ is phenyl, cyclo(lower)alkyl, indolyl, lower alkyl-indazolyl or 2,3-dihydroindolyl group, Y is single bond, lower alkylene or lower alkenylene group, and A is lower alkylene group.

DISCLOSURE OF INVENTION

As a result of an extensive study, the inventors of the present invention found some amide compounds which have strong pharmacological activities.

The amide compounds of the present invention are novel and can be represented by the formula (I):

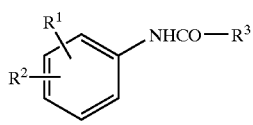

(I)

wherein $R^1$ is an N-containing heterocyclic group selected from an imidazolyl, a triazolyl, a pyridyl, a pyridazinyl, a pyrimidinyl and a pyrazinyl group, each of which may be substituted with one or more lower alkyl groups, $R^2$ is a hydrogen atom or a lower alkyl group, and $R^3$ is a phenyl group substituted with thienyl or halophenyl; a thienyl group substituted with thienyl, phenyl or halophenyl; a pyrrolyl group substituted with phenyl; a thiazolyl group substituted with phenyl; an indolyl group substituted with lower alkyl and/or halo(lower)alkyl; a fluorenyl group; or a carbazolyl group, provided that (1) the imidazolyl group for $R_1$ is substituted with one or more alkyl groups, when $R^3$ is a phenyl group substituted with thienyl; an indolyl group substituted with lower alkyl; or carbazolyl group, (2) the imidazolyl group for $R^1$ is substituted with two lower alkyl groups, when $R^3$ is a phenyl group substituted with halophenyl, or (3) $R^1$ is pyridyl, pyridazinyl, pyrimidinyl, pyrazinyl, a 4-(lower alkyl)-imidazol-1-yl or a 4,5-di(power alkyl)-imidazol-1-yl group, when $R^3$ is fluorenyl group.

Suitable salts of the compounds (I) are conventional non-toxic pharmaceutically acceptable salts and may include salts with inorganic bases, for example, alkali metals (e.g. sodium or potassium), alkaline earth metals (e.g. calcium or magnesium) or ammonia; salts with organic bases, for example, organic amines (e.g. triethylamine, pyridine, picoline, ethanolamine, triethanolamine, dicyclohexylamine or N,N'-dibenzylethylenediamine); inorganic acid addition salts (e.g. hydrochloride, hydrobromide, hydriodide, sulfate or phosphate); organic carboxylic or sulfonic acid addition salts (e.g. formate, acetate, trifluoroacetate, maleate, tartrate, methanesulfonate, benzenesulfonate or p-toluenesulfonate); salts with basic or acidic amino acids (e.g. arginine, aspartate or glutamate); and the like, and preferable examples thereof are the inorganic or organic acid addition salts.

According to the present invention, the object compounds (I) can be prepared by the following process:

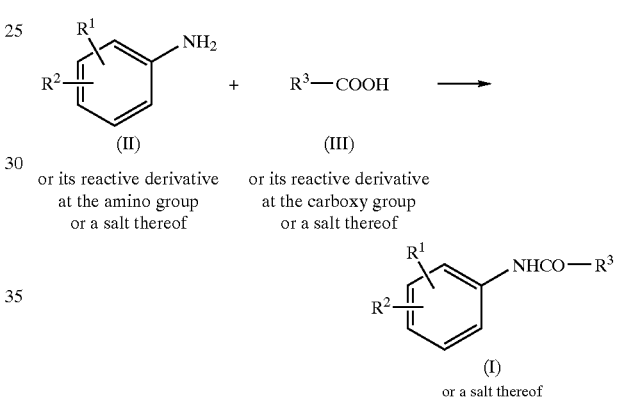

wherein $R^1$, $R^2$ and $R^3$ are each as defined above.

In the above and subsequent descriptions of the present. specification, suitable examples and illustrations of the various definitions which the present invention include within the scope are explained in detail in the following.

The term "lower" is intended to mean 1 to 6 carbon atoms, preferably 1 to 4 carbon atoms, unless otherwise indicated.

Suitable lower alkyl groups and lower alkyl moieties in the halo(lower)alkyl groups may include straight or branched ones, having 1 to 6 carbon atom(s), such as methyl, ethyl, propyl, isopropyl, butyl, t-butyl, pentyl and hexyl, and preferably the ones having 1 to 4 carbon atom(s), among which the most preferred one is methyl.

Suitable halo(lower)alkyl groups may include lower alkyl groups substituted with one or more halogen atoms such as fluoromethyl, fluoroethyl, fluoropropyl, trifluoromethyl, chloromethyl, dichloromethyl, chloroethyl, chloropropyl, bromomethyl, bromoethyl, bromopropyl, iodomethyl, iodoethyl, iodopropyl, and the like.

Suitable halophenyl groups may include fluorophenyl, difluorophenyl, chlorophenyl, dichlorophenyl, trichlorophenyl, bromophenyl, dibromophenyl, tribromophenyl, iodophenyl, and the like.

When imidazolyl, triazolyl, pyridyl, pyridazinyl, pyrimidinyl or pyrazinyl groups for $R^1$ is substituted with two or more lower alkyl groups, said lower alkyl groups may be the same or different from each other.

And also, when indolyl group for $R^3$ is substituted with two or more lower alkyl groups and/or two or more halo (lower)alkyl groups, said lower alkyl groups and halo (lower)alkyl groups may be the same or different from each other.

The process for preparing the object compounds (I) is explained in detail in the following.

The object compound (I) and its salt can be prepared by reacting a compound (II) or its reactive derivative at the amino group or a salt thereof with a compound (III) or its reactive derivative at the carboxy group or a salt thereof.

Suitable reactive derivatives at the amino group of the compound (II) may include Schiff's base type imine or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl)acetamide, bis(trimethylsilyl)urea or the like; a derivative formed by the reaction of a compound (II) with phosphorus trichloride or phosgene, and the like.

Suitable salts of the compound (II) and its reactive derivative can be referred to those as exemplified for the compound(I).

Suitable reactive derivatives at the carboxy group of the compound (III) may include the acid halides, acid anhydrides, activated amides, activated esters and the like.

Suitable examples of such reactive derivatives may be the acid chloride; the acid azide; the mixed acid anhydride with an acid such as substituted phosphoric acid [e.g. dialkylphosphoric acid, phenylphosphoric acid, diphenylphosphoric acid, dibenzylphosphoric acid or halogenated phosphoric acid], dialkylphosphorous acid, sulfurous acid, thiosulfuric acid, sulfuric acid, sulfonic acid [e.g. methanesulfonic acid], aliphatic carboxylic acid [e.g. acetic acid, propionic acid, butyric acid, isobutyric acid, pivalic acid, pentanoic acid, isopentanoic acid, 2-ethylbutyric acid or trichloroacetic acid] or aromatic carboxylic acid [e.g. benzoic acid]; symmetrical acid anhydride; activated amide with imidazole, 4-substituted imidazole, dimethylpyrazole, triazole or tetrazole; or activated ester [e.g. cyanomethyl ester, methoxymethyl ester, dimethyliminomethyl [$(CH_3)_2N^*=CH$-] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester or 8-quinolyl thioester], or ester with an N-hydroxy compound [e.g. N,N-dimethylhydroxylamine, 1-hydroxy-2-(1H)-pyridone, N-hydroxysuccinide, N-hydroxyphthaimide or 1-hydroxy-1H-benzotriazole], and the like.

The reactive derivative can optionally be selected from the above according to the kind of the compound (III) to be used.

Suitable salts of the compound (III) and its reactive derivative may be the base salts such as alkali metal salts [e.g. sodium salt or potassium salt], alkaline earth metal salts [e.g. calcium salt or magnesium salt], ammonium salts, organic base salts [e.g. trimethylamine salt, triethylamine salt, pyridine salt, picoline salt, dicyclohexylamine salt or N,N'-dibenzylethylenediamine salt], or the like, and acid addition salts as exemplified for the compound (I).

The reaction is usually carried out in a conventional solvent such as water, alcohol [e.g. methanol or ethanol], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction, or a mixture thereof.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N-N'-diethylcarbodiiide, N,N'-diisopropylcarbodiimide; N-ethyl-N'-(3-dimethylaminopropyl) carbodiimide; N,N'-carbonylbis-(2-methylimidazole); pentamethyleneketene-N-cyclohexylimine; diphenylketene-N-cyclohexylixine; ethoxyacetylene; 1-alkoxy-1-chloroethylene; triallyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)-isoxazolium hydroxide intramolecular salt; benzotriazol-1-yloxy-tris(dimethylamino) phosphonium hexafluorophosphate; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine or the like, The reaction is usually carried out under cooling to warming, although the reaction temperature is not critical.

The object compound (I) of the present invention can be isolated and purified in a conventional manner, for example extraction, precipitation, fractional crystallization, recrystallization, chromatography and the like.

The object compound (I) thus obtained can be converted to its corresponding salt by the conventional method.

The object compound (I) and salts thereof may include solvates [e.g., enclosure compound (e.g., hydrate, etc.)].

Among the starting compounds (II) and (III), novel compounds can be prepared by the method described in the following Examples or similar method thereto.

In order to exhibit the usefulness of the present invention, the activities of the compounds (I) are shown in the following.

Test Method.

[$^3$H]-mesulergine Binding

The affinity of the test drugs for the $5-HT_{2c}$ binding site can be determined by assessing their ability to displace [$^3$H]-mesulergine in the rat prefrontal cortex. The method employed was similar to that of Pazos et al, 1984.

The membrane suspension (500 $\mu$l) was incubated with [$^3$H]-mesulergine (1 nM) in Tris HCl buffer containing $CaCl_2$ 4 mM and ascorbic acid 0.1 % (pH 7.4) at 37° C. for 30 minutes. Non-specific binding was measured in the presence of mianserin (1 $\mu$M). 30 nM spiperone was used to prevent binding to $5-HT_{2A}$ sites. Test drugs ($10^{-6}$ M) were added in a volume of 100 $\mu$l. The total assay volume was 1000 $\mu$l. Incubation was stopped by rapid filtration using a Brandel cell harvester and radioactivity measured by scintillation counting.

The $IC_{50}$ values were determined using a four parameter logistic program (DeLean 1978) and the phi (the negative logarithm of the inhibition constant) calculated from the Cheng Prusoff equation where:

$$Ki = \frac{IC_{50}}{1 + C/Kd}$$

$Ki$ = inhibition constant $C$ = concentration of $[^3H]$-mesulergine $Kd$ = affinity of mesulergine for 5-HT$_{2c}$ binding site.

Test Compounds:

(1) N-(1-Methyl-1H-indol-5-yl)-N'-(3-pyridyl)urea (reference compound)
(2) N-(3-(yridin-3-yl)phenyl)-9H-fluorene-1-carboxamide (Example 1)
(3) N-(3-(pyrimidin-5-yl)phenyl)-9H-fluorene-1-carboxamide (Example 2)
(4) N-(3-(pyridazin-4-yl)phenyl)-9H-fluorene-1-carboxamide (Example 6)

Test Result:

| Compound | Inhibition (%) |
|---|---|
| (1) | 21 |
| (2) | 74 |
| (3) | 92 |
| (4) | 64 |

As shown in above, the object compounds (I) of the present invention exhibit pharmacological activities such as 5-HT antagonism, especially, 5-HT$_{2c}$ antagonism, and therefore are useful as 5-HT antagonist for treating or preventing central nervous system (CNS) disorders such as anxiety, depression, obsessive compulsive disorders, migraine, anorexia, Alzheimer's disease, sleep disorders, bulimia, panic attacks, withdrawal from drug abuse (e.g., with cocaine, ethanol, nicotine and benzodia pines), schizophrenia, and also disorders associated with spinal trauma and/or head injury such as hydrocephalus, and the like.

For therapeutic or preventive administration, the object compounds (I) of the present invention are used in a form of conventional pharmaceutical preparation which contains said compound as an active ingredient, in admixture with pharmaceutically acceptable carriers such as an organic or inorganic solid or liquid excipient which is suitable for oral, parenteral and external administration. The pharmaceutical preparations may be in a solid form such as tablet, granule, powder or capsule, or in a liquid form such as solution, suspension, syrup, emulsion or lemonade.

If needed, there may be included in the above preparations auxliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol and the like.

While the dosage of the compound (I) may vary from and also depend upon the age, conditions of the patient, kind of diseases or conditions, kind of the compound (I) to be applied, etc., in general, 0.01–500 mg of the compound (I) may be administered to a patient per day.

An average single dose of about 0.05 mg, 0.1 mg, 0.25 mg, 0.5 mg, 1 mg, 20 mg, 50 mg, 100 mg of the compound (I) may be used in treating the diseases.

The following Examples are given for illustrating the present invention, but it is to be noted that the scope of the present invention is not limited by these Examples.

BEST MODE FOR CARRYING OUT THE INVENTION

The following Examples are given only for the purpose of illustrating the present invention in more detail.

EXAMPLE 1

To a suspension of 3-pyridin-3-yl)aniline (0.17 g) and pyridine (0.24 ml) in dichloromethane (3 ml) was dropwise added a solution of the fluorene-1-carbonyl chloride (0.23 g) in dichloromethane (2 ml) followed by stirring for 2 hours. The mixture was diluted with dichloromethane and washed with an aqueous solution of sodium hydrogen carbonate and brine. The separated organic layer was dried over sodium sulfate and evaporated under reduced pressure. The residue was purified by a silica gel column chromatography eluting with 2% methanol in dichloromethane to give N-(3-(pyridin-3-yl)phenyl)-9H-fluorene-1-carboxamide (0.317 g, 87.6%).

NMR (DMSO-d$_6$, δ):4.23 (2H, s), 7.3–b 7.7 (7H, m), 7.78 (1H, d, J=7.7 Hz), 7.8–8.1 (4H, m), 8.18 (1H, s), 8.60 (1H, d, J=4.8 Hz), 8.88 (1H, s), 10.47 (1H, s) APCI-Mass m/z: 363 (M$^+$+1).

EXAMPLE 2

To a suspension of 3-(pyrimidin-5-yl)aniline (0. 17g) and pyridine (0.24 ml) in dichloromethane (3 ml) was dropwise added a solution of the fluorene-1-carbonyl chloride (0.23 g) in dichloromethane (5 ml) followed by stirring for 2 hours. The mixture was diluted with dichloromethane and washed with an aqueous solution of sodium hydrogen carbonate and brine. The separated organic layer was dried over sodium sulfate and evaporated. The residue was purified by a silica gel column chromatography eluting with 2% methanol in dichloromethane to give N-[3-(pyrimidin-5-yl)phenyl] fluorene-1-carboxamide (0.222 g, 61.2 %).

NMR PMSO-d$_6$, δ): 4.23 (2H, s), 7.3–7.5 (2H, m), 7.5–7.7 (4H, m), 7.78 (1H, d, J=8.0 Hz), 7.8–8.1 (2H, m), 8.13 (1H, d, J 7.7 Hz), 8.21 (1H, s), 9.12 (2H, s), 9.23 (1H. s), 10.51 (1H, s) APCI-Mass m/z: 364 (M$^+$+1).

EXAMPLE 3

To a suspension of 9H-carbazole-1-carboxylic acid (106 mg) and 1-hydroxybenzotriazole (81 mg) in dichloromethane (2 ml) was added 1-ethyl-3-(3-dimethylaminopropyl)carbodiimide hydrochloride (144 mg) and the mixture was stirred for 15 minutes. After adding 3-(1,2-dimethylimidazol-5-yl)aniline (94 mg) and 4-dimethylaminopyridine (92 mg), the mixture was stirred for 60 hours. The residue was evaporated under reduced pressure and purified by a silica gel column chromatography eluting with 2% methanol in dichloromethane to give N-[3-(2,3-dimethyl-3H-imidazol-4-yl)-phenyl]-9H-carbazole-1-carboxamide (101 mg, 53.2%).

NMR PMSO-d$_6$, δ): 2.37 (3H, s), 3.59 (3H, s), 6.90 (1H, s), 7.2–7.6 (5H, m), 7.71 (1H, d, J=8.0 Hz), 7.89 (1H, d, J=8.2 Hz), 7.96 (1H, s), 8.11 (1H, d, J=7.4 Hz), 8.18 (1H, d, J=7.7 Hz), 8.38 (1H, d, J=7.7 Hz), 10.47 (1H, s), 11.49 (1H, s) APCI-Mass m/z; 381 (M$^+$1).

Preparation 4(1)

To a suspension of 3,6-dichloropyridazine (2.98 g), 3-nitrophenylboronic acid (1.67 g) and tetralis (triphenylphosphine)-palladium (578 mg) in 1,2- dimethoxyethane (30 ml) was added an aqueous solution of sodium carbonate (2M, 15 ml), and the mixture was stirred at 80° C. for 3 hours. The mixture was diluted with ethyl acetate, and then washed with water and brine. The organic layer was dried over magnesium sulfate and evaporated under reduced pressure. The residue was purified by a silica gel column chromatography eluting with 30% ethyl acetate in n-hexane to give 3-chloro-6-(3-nitro-phenyl)-pyridazine (0.246 g, 10.4%).

NMR (DMSO-$d_6$, δ): 7.88 (1H, t, J=8.1 Hz), 8.13 (1H, d, J=9.0 Hz), 8.41 (1H, dt, J=6.8 Hz, 1.2 Hz), 8.54 (1H, d, J=9.0 Hz), 8.6–8.8 (1 H,m), 8.97 (1H, t, J=1.2 Hz) APCI-Mass m/z : 236 ($M^+$+1).

Preparation 4(2)

A suspension of 3-chloro6-(3-nitro-phenyl)pyridazine (0.34 g) in tetrahydrofuran (5 ml) and ethanol (5 ml) was hydrogenated over palladium on carbon (10% w/w, 50% wet, 100 mg) under hydrogen atmosphere for 10 hours. The catalyst was filtered off and the filtrate was evaporated under reduced pressure. The residue was diluted with ethyl acetate and an aqueous solution of sodium hydrogen carbonate. The separated organic layer was washed with brine, dried over magnesium sulfate and evaporated under reduced pressure to give 3-pyridazin-3-yl-phenylamine (155 mg, 62.8%).

NMR (DMSO-$d_6$, δ): 5.29 (2H, broad s), 6.72 (1H, t, J=2.8 Hz), 7.1–8.0 (4H, ml, 8.04 (1H, d, J=8.6 Hz), 9.16 (1H, dd, J=5.0 Hz, 1.6 Hz) APCI-Mass m/z: 172 ($M^+$+1).

EXAMPLE 4

To a suspension of 1-fluorenecarboxylic acid (184 mg) and oxalyl chloride (0.2 ml) in dichloromethane (4 ml) was added N,N-dimethylformamide (0.01 ml), and the mixture was stirred for 2 hours. The resultant solution was evaporated to give a crude acid chloride. To a suspension of 3-pyridazin-3-yl-phenylamine (150 mg) and pyridine (0.21 ml) in dichloromethane (2 ml) was dropwise added a solution of the acid chloride obtained above in dichloromethane. (5 ml) followed by stirring for an hour. The mixture was diluted with dichloromethane and washed with an aqueous solution of sodium hydrogen carbonate and brine. The separated organic layer was dried over sodium sulfate and evaporated under reduced pressure. The residue was purified by a silica gel column chromatography eluting with 2% methanol in dichloromethane to give N-(3-(pyridazin-3-yl) phenyl)-9H-fluorene-1-carboxamide (44 mg, 13.8%).

NMR (DMSO-$d_6$, δ): 4.24 (2H, s). 7.3–7.5(2H, m), 7.5–7.7 (3H, m), 7.7–7.9 (3H, m), 7.99 (1H, dd, J=7.0 Hz, 1.8 Hz), 8.1–8.3 (2H, m), 8.70 (1H, t, J=3.6 Hz), 9.24 (1H, dd, J=4.9 Hz, 1.5 Hz), 10.54 (1H, s) APCI-Mass m/z: 364 ($M^+$+1).

Preparation 5(1)

To a suspension of 2-chloropyrazine (1.14 g), 3-nitrophenylboronic acid (2.00 g) and tetrakis (triphenylphosphine)-palladium (346 mg) in 1,2-dimethoxyethane (30 ml) was added an aqueous solution of sodium carbonate (2M, 12 ml) followed by stirring at 80° C. for 18 hours. The mixture was diluted with dichloromethane and washed with water and brine. The organic layer was dried over magnesium sulfate and evaporated under reduced pressure. The residue was triturated with methanol and collected by filtration. The obtained product was washed with methanol and diisopropyl ether and dried to give 2-(3-nitrophenyl)pyrazine (1.78 g, 88.6%).

NMR (CDCl, δ): 7.26 (1H, s), 7.67 (1H, t, J=8.0 Hz), 8.36 (1H, dt, J=7.7 Hz, 1.5 Hz), 8.63 (1H, d, J=2.4 Hz), 8.70 (1H, t, J=4.0 Hz), 8.93 (1H, t, J=4.0 Hz), 9.13 (1H, t, J=1.5 Hz) APCI-Mass m/z: 202 ($M^+$+1).

Preparation 5(2)

A suspension of 2-(3-nitrophenyl)pyrazine (500 mg) in tetrahydrofuran (5 ml) and ethanol (5 ml) was hydrogenated over palladium on carbon (10% w/w, 50% wet, 200 mg) under hydrogen atmosphere for 6 hours. The catalyst was filtered off and the filtrate was evaporated. The residue was crystallized from dichloromethanediisopropyl ether to give 3-(pyrazin-2-yl)aniline (410 mg, 96.5%).

NMR (CDCl$_3$, δ): 3.82(2H, s), 6.81 (1H, dt, J=6.0 Hz, 1.2 Hz), 7.3–7.6 (3H, m), 8.49 (1H, d, J=2.5 Hz), 8.60 (1H, t, J=1.3 Hz), 9.00 (1H, d, J=1.5 Hz) APCI-Mass m/z: 171 ($M^+$+1).

EXAMPLE 5

To a suspension of 3-(pyrazin-2-yl)aniline (0.12g) and pyridine (0.17ml) in dichloromethane (3ml) was dropwise added a solution of the fluorene-1-carbonyl chloride (0.16 g) in dichloromethane (3 ml) followed by stirring for 2 hours. The mixture was diluted with dichloromethane and washed with an aqueous solution of sodium hydrogen carbonate and brine. The separated organic layer was dried over sodium sulfate and evaporated under reduced pressure. The residue was purified by a silica gel column chromatography eluting with 2% methanol in dichloromethane to give N-(3-(pyrazin-2-yl)phenyl)-9H-fluorene-1-carboxamide (0.193 g; 76.0%).

NMR (DMSO-$d_6$, δ): 4.24 (2H, s), 7.3–7.7 (5H, m), 7.79 (1H, d, J=7.6 Hz), 7.8–8.1 (3H, m), 8.13 (1H, d, J=6.8 Hz), 8.68.7 (2H, m), 8.76 (1H, t, J=1.2 Hz), 9.23 (1H, d, J=1.5 Hz), 10.52 (1H, s) APCI-Mass m/z: 364 ($M^{30}$ +1).

Preparation 6(1)

A suspension of 3-nitrobenzyl cyanide (1.62 g), glyoxylic acid monohydrate (1.38 g) and potassium carbonate (3.59 g) in methanol (20 ml) was stirred for 5 hours. The precipitate was collected by filtration, washed with dichloromethane and dried. The precipitate was suspended in water and stirred for an hour. The insoluble material was collected by filtration and dried to give 3-cyano-3-(3-nitro-phenyl)-acrylic acid potassium salt (2.18 g, 85.2%).

ESI-Mass m/z: 217 (M–$K^+$) NMR (DMSO-$d_6$, δ): 7.36 (1H, s), 7.73 (1H, t, J=8.0 Hz), 8.10 (1H, d, J=7.9 Hz), 8.24 (1H, d, J=7.9Hz), 8.62 (lH, s)

Preparation 6(2)

To a suspension of.3-cyano-3-(3-nitro-phenyl)-acrylic acid potassium salt (1.28 g) in formic acid (10 ml) and water (1 ml) was added sulfuric acid (1 ml), and the mixture was refluxed for 3 hours. After cooling, the mixte was poured into water. The resulting precipitate was collected by filtration and dried to give 3-(3-nitrophenyl)-furan-2,5-dione (0.69 g).

NMR (CDCl$_3$, δ): 7.24 (1H, d, J=8.9 Hz), 7.76 (1H, d, J=8.1 Hz), 8.3–8.5 (2H, m), 8.81 (1H,s) APCI-Mass m/z: 220 ($M^+$+1).

Preparation 6(3)

To a suspension of 3-(3-nitro-phenyl)-f ran-2,5-dione (673 mg) in acetic acid (7 ml) was added hydrazine hydrate (0.18 ml), and the mixture was refluxed for S hours. The mixture was poured into water. The resulting precipitate was collected by filtration and dried to give 4-(3-nitro-phenyl)-1,2-dihydro-pyridazine-3,6-dione (0.68 g, 95.0%). NMR (0MSO-$d_6$, δ): 7.43 (1H, s), 7.6–8.4 (3H, m), 8.81 (1H, s), 11.04 (1H, broad s), 12.31 (1H, broad s) APCI-Mass m/z: 234 ($M^+$+1).

Preparation 6(4)

A suspension of 4-(3nitro-phenyl)-1,2-dihydropyridazine-3,6-dione (668 mg) in phosphorus oxychloride (6 ml) was refluxed for 2 hours. The mixture was concentrated under reduced pressure and diluted with ethyl acetate. The solution was washed with an aqueous solution of sodium hydrogen carbonate and brine and dried over magnesium sulfate. The organic layer was evaporated under reduced pressure. The residue was purified by a silica gel column chromatography eluting with dichloromethane to give 3,6-dichloro-4-(3-nitro-phenyl)pyridazine (385 mg, 49.9%). NMR (CDCl$_3$, δ): 7.26(1H, s), 7.57 (1H, s), 7.76 (1H, t, J=8.1 Hz), 7.86 (1H d, J=7.9 Hz), 8.4–8.6 (2H, m) APCI-Mass m/z: 270 (M$^+$+1).

Preparation 6(5)

A suspension of 3,6dichloro4-(3-nitro-phenyl)pyridazine (0.19 g) and sodium hydrogen carbonate (147 mg) in tetrahydrofuran (2 ml) and ethanol (5 ml) was hydrogenated over palladium on carbon (10% w/w, 50% wet, 100 mg) under hydrogen atmosphere for 3 hours. The catalyst was filtered off, and the filtrate was evaporated. The residue was diluted with ethyl acetate and an aqueous solution of sodium hydrogen carbonate. The separated organic layer was washed with brine and dried over potassium carbonate. The organic layer was evaporated under reduced pressure to give 3-(pyridazin-4-yl)phenylamine (106 mg, 88.3%).

NMR PMSO-d$_6$, δ): 5.35 (2H, broad s), 6.72 (1H, t, J=7.6 Hz), 7.0–7.2 (2H, m), 7.20 (1H, t, J=8.0 Hz), 7.85 (1H, dd, J=5.6 Hz, 2.4 Hz), 9.23 (H, d, J=5.6 Hz), 9.49 (1H, s) APCI-Mass m/z: 172 (M$^+$+1).

EXAMPLE 6

To a suspension of 1-fluorenecarboxylic acid (120 mg) and oxalyl chloride (0.12 ml) in dichloromethane (2.5 ml) was added N,N-dimethylformamide (0.01 ml) and the mixture was stirred for 2 hours. The resultant solution was evaporated to give a crude acid chloride. To a suspension of 3-(pyridazin-4-yl)phenylamine (98 mg) and pyridine (0.14 ml) in dichloromethane (2 ml) was dropwise added a solution of the acid chloride obtained above in dichloromethane (5 ml), and the mixture was stirred for an hour. The mixture was diluted with dichloromethane and washed with an aqueous solution of sodium hydrogen carbonate and brine. The separated organic layer was dried over sodium sulfate and evaporated under reduced pressure. The residue was purified by a silica gel column chromatography eluting with 2% methanol in dichloromethane to give N-(3-(pyridazin-4-yl)-phenyl)-9H-fluorene-1-carboxamide (133 mg, 63.9%)

NMR (DMSO-d$_6$, δ): 4.23 (2H, s), 7.3–7.7 (6H, m), 7.79 (1H, d, J=7.0 Hz), 7.9–8.1 (3H, m), 8.14 (1H, d, J=6.9 Hz), 8.34 (1H, s), 9.32 (1H, d, J=5.5 Hz), 9.60(1H, s), 10.56(1H, s) APCI-Mass m/z: 364 (M$^+$+1).

Preparation 7

To a solution of 2-(3-methoxycarbonylphenyl)thiophene (1.29 g) in methanol (15 ml) and tetrahydrofuran (5 ml) was added an aqueous solution of sodium hydroxide (1N, 8.87 ml) followed by stirring for 2 hours at 60° C. To the mixture was added hydrochloric acid (1N, 10 ml). The resulting precipitate was collected by filtration and dried to give 2-(3-carboxyphenyl)thiophene (1.13 g, 93.4%).

NMR (DMSO-d$_6$, δ): 7.17 (1H, t, J=4.4 Hz), 7.5–7.7(3H, m), 7.87 (1H, d, J=7.8 Hz), 7.93 (1H, d, J=7.8 Hz), 8.15 (1H, s), 13.19 (1H, broad s) ESI-Mass m/z: 203 (M$^+$−1).

EXAMPLE 7

To a suspension of 3-(2-thienyl)benzoic acid (102 mg) and oxalyl chloride (0.2 ml) in dichloromethane (2 ml) was added N,N-dimethylformamide (0.01 ml), and the mixture was stirred for an hour. The resultant solution was evaporated to give a crude acid chloride. To a suspension of 3-(1,2-dimethylimidazol-5-yl)aniline (94 mg) and pyridine (0.12 ml) in dichloromethane (2 ml) was dropwise added a solution of the acid chloride obtained above in dichloromethane (2 ml), and the mixture was stirred for 12 hours. The mixture was diluted with dichloromethane and washed with an aqueous solution of sodium hydrogen carbonate and brine. The separated organic layer was dried over sodium sulfate and evaporated under reduced pressure. The residue was purified with a silica gel column chromatography eluting with 3% methanol in dichloromethane to give N-[3-(2,3-dimethyl-3H-idazol-4-yl )-phenyl]-3-(thiophen-2-yl) benzamide (140 mg, 74.9%).

NMR (DMSO-d$_6$, δ): 2.36 (3H,s), 3.59 (3H, s), 6.89 (1H, s), 7.1–7.3 (2H, m), 7.44 (1H, t, J=7.9 Hz), 7.6–7.8 (3H, m), 7.79 (1H, d, J=8.0 Hz), 7.8–8.0 (3H, m), 8.19 (1H, s), 10.45 (1H, s) APCI-Mass m/z: 374 (M$^+$+1).

EXAMPLE 8

To a suspension of 9H-carbazole-1-carboxylic acid (422 mg) and 1-hydroxybenzotriazole (324 mg) in dichloromethane (10 ml) was added 1-ethyl-3-(3-dimethylaminopropyl)carbodiimide hydrochloride (575 mg), and the mixture was stirred for 15 minutes. After adding 3-(pyrimidin-5-yl)aniline (360 mg) and 4-dimethylaminopyridine (367 mg), the mixture was stirred for 48 hours. The residue was evaporated under reduced pressure and purified by a silica gel column chromatography eluting with 2% methanol in dichloromethane to give N-(3-i din-5-yl)-phenyl)-9H-carbazole-1-carboxamide (314 mg, 43.1%).

NMR (DMSO-d$_6$, δ): 7.20(1H, t, J=7.4 Hz), 7.33 (1H, t, J=7.7 Hz), 7.42 (1H, t, J=7.6 Hz), 7.58 (2H, d, J=5.1 Hz), 7.72 (1H, d, J=8.0 Hz), 7.9–8.1 (1H, m),8.17 (2H, dd, J=7.4 Hz, 4.0 HZ), 8.35 (1H, 5), 8.39 (1H, d, J=7.5Hz), 9.15 (2H, s), 9.23 (1H, s), 10.56 (1H, s), 11.54 (1H, s) APCI-Mass m/z: 365 (M$^+$+1).

EXAMPLE 9

To a suspension of 9H-carbazole-1-carboxylic acid (148 mg) and 1-hydroxybenzothiazole (114 mg) in dichloromethane (3 ml) was added 1-ethyl-3-(3-dimethylaminopropyl)carbodiimide hydrochloride (201 mg) and the mixture was stirred for 15 minutes. After adding 3-(1,2,4-triazol-1-yl)aniline (123 mg) and 4-dimethylaminopyridine (128 mg), the mixture was stirred for 24 hours. The mixture was evaporated under reduced pressure and purified by a silica gel column chromatography eluting with 2% methanol in dichloromethane to give N-[3-(1,2,4-triazol-1-yl)-phenyl]-9H-carbazole-1-carboxamide (103 mg, 41.5%).

NMR (DMSO-d$_6$, δ): 7.20(1H, t, J=7.3 Hz), 7.32 (1H, t, J=7.5 Hz), 7.42 (1H, t, J=7.3 Hz), 7.5–7.7 (2H, m), 7.73 (1H, d, J=8.2 Hz), 7.86 (1H, d, J=7.3 Hz), 8.1–8.3 (2H, m), 8.28 (1H, s), 8.40 (1H, d, J=7.5 Hz), 8.61 (1H, s), 9.30 (1H, s), 10.64 (1H, s), 11.57 (1H, s) APCI-Mass m/z: 354 (M$^+$+1).

Preparation 10(1)

To a suspension of 2-bromo-5-methoxycarbonylthiophene (1.11 g) and phenylboronic acid (0.79 g) and tetrakis(triphenylphosphine)-palladium (289 mg) in 1,2-dimethoxyethane (10 ml) was added an aqueous solution of sodium carbonate (2M, 6.5 ml) followed by stirring at 80° C. for 18 hours. The mixture was diluted with dichloromethane and washed with water and brine. The mixture was dried over magnesium sulfate and evaporated under reduced pressure. The residue was triturated with methanol. The resulting precipitate was collected by filtration, washed with methanol and diisopropyl ether and dried to give 2-methoxycarbonyl-5-phenylthiophene (918 mg, 84.2%).

NMR (CDCl$_3$, δ): 3.84 (3H, s), 7.4–7.6 (3H, m), 7.62 (1H, d, J=4.0 HZ), 7.7–7.9 (2H, m), 7.81 (1H, d, J=4.0 Hz) APCI-Mass m/z : 219 (M$^+$+1).

Preparation 10(2)

To a solution of 2-methoxycarbonyl-5-phenylthiophene (437 mg) in methanol (5 ml) and tetrahydrofuran (5 ml) was added an aqueous solution of sodium hydroxide (IN, 3 ml) followed by stirring for 2 hours. To the mixture was added hydrochloric acid (IN, 5 ml). The precipitate was collected by filtration and dried to give 5-phenylthiophene-2-carboxylic acid (397 mg, 97.1%).

NMR (PMSO-d$_6$, δ): 7.3–7.5 (3H, m), 7.58 1(1H, d, J=3.9 Hz), 7.6–7.8 (3H, m), 13.15 (1H, broad s) ESI-Mass m/z: 203 (M$^+$−1).

EXAMPLE 10

To a suspension of 5-phenylthiophene-2-carboxylic acid (102 mg) and oxalyl chloride (0.2 ml) in dichloromethane (2 ml) was added N,N-dimethylformamide (0.01 ml), and the mixture was stirred for an hour. The resultant solution was evaporated under reduced pressure to give a crude acid chloride. To a suspension of 3-(1,2-dimethylimidazol-5-yl)aniline (94 mg) and pyridine (0.12 ml) in dichloromethane (2 ml) was dropwise added a solution of the acid chloride obtained above in dichloromethane (2 ml) followed by stirring for 12 hours. The mixture was diluted with dichloromethane and washed with an aqueous solution of sodium hydrogen carbonate and brine. The separated organic layer was dried over sodium sulfate and evaporated under reduced pressure. The residue was purified by a silica gel column chromatography eluting with 3% methanol in dichloromethane to give N-[3-(2,3-dimethyl-3H-imidazol4-yl)-phenyl]-5-phenyl-thiophene-2-carboxamide (155 mg, 82.9%).

NMR PMSO-d$_6$, δ): 2.36 (3H,s), 3.57 (3H, s), 6.89 (1H, s), 7.17 (1H, d, J=7.8 HZ), 7.4–7.6 (4H, m), 7.64 (1H, d, J=4.0 Hz), 7.7–7.9 14H, m), 8.04 (1H, d, J=4.0 Hz), 10.34 (1H, s) APCI-Mass m/z: 374 (M$^+$+1).

Preparation 11 (1)

To a suspension of 5-bromopyrimidine (1.59 g), 4-methyl-3-nitrophenylboronic acid (2.35 g) and tetrakis (triphenylphosphine)-palladium (578 mg) in 1,2-dimethoxyethane (20 ml) was added an aqueous solution of sodium carbonate (2M, 13 ml) followed by stirring at 80° C. for 24 hours. The mixture was diluted with dichloromethane and washed with water and brine. The organic layer was dried over magnesium sulfate and evaporated under reduced pressure. The residue was triturated with methanol. The resulting precipitated was collected by filtration, washed with methanol and diisopropyl ether and dried to give 5-(4-methyl-3-nitrophenyl)-pyrimidine (918 mg, 84.2%).

NMR (CDCl3, 6): 2.56 (3H, s), 7.68 (1H, d, J=8.0 Hz), 8.10 (1H, dd, J=8.0 Hz, 1.8 Hz), 8.42 (1H, d. J=1.8 Hz), 9.23 (3H, s) APCI-Mass m/z: 216 (M$^+$+1).

Preparation 11 (2)

A suspension of 5-(4-methyl-3-nitrophenyl)-pyrimidine (258 mg) in tetrahydrofuran (5ml) and methanol (5 ml) was hydrogenated over palladium on carbon (10% w/w, 50% wet, 130 mg) under hydrogen atmosphere for 4 hours. The catalyst was filtered off and the filtrate was evaporated to give 5-(3-amino4-methylphenyl)pyrimidine(410 mg, 96.5%).

NMR (CDCl$_3$, δ): 2.11 (3H, s), 5.05 (2H, s), 6.87 (1H, dd, J=7.6 Hz, 1.8 Hz), 6.96 (1H, d, J=1.8 Hz), 7.07 (1H, d, J=7.6 Hz), 8.98 (2H, s), 9.12 (1H, s) APCI-Mass m/z: 186 (M$^+$+1).

EXAMPLE 11

To a suspension of 9H-carbazole-1-carboxylic acid (148 mg) and 1-hydroxybenzotriazole (114 mg) in dichloromethane (3 ml) was added 1-ethyl-3-(3-dimethylaminopropyl)carbodiinide hydrochloride (201 mg), and the m e was stirred for 15 minutes. After adding 5-(3-amino-4-methylphenyl)pyrimdine (136 mg) and 4dimethylaminopyridine (128 mg), the mixture was stirred for 24 hours. The mixture was evaporated under reduced pressure and the residue was purified by a silica gel column chromatography eluting with 2% methanol in dichloromethane to give N-[6methyl-3-(pyrimidin-5-yl)-phenyl]-9H-carbazole-1-carboxamide (89 mg, 33.6%).

NMR (DMSO-d$_6$, δ): 2.40 (3H, s), 7.20(1H, t, J=7.4 Hz), 7.32 (1H, t, J=7.6 Hz), 7.4–7.6 (2H, m), 7.6–7.8 (2H, m), 7.96 (1H, s), 8.17 (2H, d, J=77 Hz), 8.39 (1H, d, J=7.6 Hz),9.17 (2H, s), 9.19 (1H, s), 10.19 (1H, s), 11.46 (1H, s) APCI-Mass m/z: 379 (M$^+$+1).

EXAMPLE 19

To a suspension of 2-trifluoromethyl-3-methylindole-7-carboxylic acid (122 mg) and 3-(1,2-dimethyiimldazol-5-yl)aniline (94 mg) in dichloromethane (3 ml) were added 1-ethyl-3-(3-dimethylamiopropyl)carbodiimide hydrochloride (144 mg) and 4-diethylaminopyridine (30 mg). The mixture was stirred at ambient temperature for 18 hours and diluted with dichloromethane. The solution was washed with water and brine, dried over magnesium sulfate and evaporated under reduced pressure. The residue was purified by a silica gel column chromatography eluting with 2% methanol in dichloromethane to give N-[3-(1,2-dimethyl-1H-imidazol-5-yl)-phenyl]-3-methyl-2-trifluoromethyl-1H-indole-7-carboxamide (130 mg,63.1%)

NMR (DMSO-$_6$, δ): 2.36 (3H, s), 2.44 (3H, s), 3.57 (3H, s), 6.88 (1H, s), 7.17 (1H, d, J=8.0 Hz), 7.31 (H, d, J=8.0 Hz), 7.45 (1H, t, J =7.8 Hz), 7.82 (1H, d, J=8.0 Hz), 7.9–8.1 (3H, m), 10.50 (1H, s), 11.48 (1H, s) APCI-Mass m/z: 413 (M$^+$+1).

EXAMPLE 13

To a suspension of 2,3-dimethylindole-7-carboxylic acid (95 mg) and 3-(1,2-dimethylimidazol-5-yl)aniline (94 mg) in dichloromethane (3 ml) were added 1-ethyl-3-(3-dimethylaminopropyl)carbodiimide hydrochloride (144 mg) and 4-dimethylaminopyridine (30 mg). The mixture was stirred at ambient temperature for 18 hours and diluted with dichloromethane. The solution was washed with water and brine, dried over magnesium sulfate and evaporated under reduced pressure. The residue was purified by a silica gel column chromatography eluting with 3% methanol in dichloromethane to give N-[3-(1,2-dimethyl-1H-imidazol-5-yl)-phenyl]-2,3-dimethyl-lH-indole-7-carboxamide (73 mg, 40.8%).

NMR (DMSO-$_6$, δ): 2.18 (3H, s), 2.37 (6H, s), 3.57 (3H, s), 6.88 (1H, s), 7.06 (1H, d, J=7.6 HZ), 7.15 (1H, d, J=10.1 Hz), 7.44 (1H, d, J=7.9 Hz), 7.61 (1H, d, J=7.6 Hz), 7.72 (1H, d, J=7.3 Hz), 7.85 (1H, d, J=8.2 Hz), 7.92 (1H, s), 10.30 (1H, s), 10.76 (1H, s) APCI-Mass m/z: 359 (M$^+$+1).

EXAMPLE 14

To a suspension of 2-trifluoromethyl-3-methylindole-7-carboxylic acid (122 mg) and 3-(pyrimidin-5-yl)aniline (86 mg) in dichloromethane (3 ml) were added 1-ethyl-3-(3-dimethylaminopropyl)carbodiimide hydrochloride (144 mg) and 4-dimethylaminopyridine (30 mg). The mixture was stirred at ambient temperature for 18 hours and diluted with dichloromethane. The solution was washed with water and brine, dried over magnesium sulfate and evaporated under reduced pressure. The residue was purified by a silica gel column chromatography eluting with 2% methanol in dichloromethane to give N-[3-(pyrimidin-5-yl)-phenyl]-3-methyl-2-trifluoromethyl-1H-indole-7-carboxamide (106 mg, 53.5%).

NMR (DMSO-$d_6$, δ): 2.45 (3H, s), 7.31 (1H, t, J=7.7 Hz), 7.4–7.6 (2H, m), 7.9–8.1 (3H, m), 8.26 (1H, s), 9.13 (2H, s), 9.23 (1H, s), 10.59 (1H, s), 11.49 (1H, s) APCI-Mass m/z: 397 ($M^+$+1).

EXAMPLE 15

To a suspension of 3-(4-fluorophenyl)benzoic acid (151 mg) and 3-(1,2-dimethylimidazol-5-yl)aniline (131 mg) in dichloromethane (5 ml) were added 1-ethyl-3-(3-dimethylaminopropyl)carbodiimide hydrochloride (201 mg) and 4-dimethylaminopyridine (43 mg). The mixture was stirred at ambient temperature for 18 hours and diluted with dichloromethane. The solution was washed with water and brine, dried over magnesium sulfate and evaporated under reduced pressure. The residue was purified by a silica gel column chromatography eluting with 3% methanol in dichloromethane to give N-[3-(2,3 dimethyl-3H-imidazolyl)-phenyl]-4'-fluoro-biphenyl-3-carboxamide (240 mg, 88.9%).

NMR (DMSO-$d_6$, δ): 2.36(3H, s), 3.57 (3H, s), 6.88 (1H, s), 7.17 (1H, d, J=7.7 Hz), 7.35 (2H, t, J=8.9 Hz), 7.45 (1H, t, J=7.9 Hz), 7.63 (1H, t, J=7.7 Hz), 7.8–8.1 (6H, m), 8.21 (1H, s), 10.43 (1H, s) ESI-Mass m/z: 386 ($M^+$+1).

Preparation 16(1)

To a suspension of 2-bromo-5-methoxycarbonylthiophene (1.11 g), 4-fluorophenylboronic acid (0.91 g) and tetrakis(triphenylphosphine)palladium (289 mg) in 1,2-dimethoxyethane (10 ml) was added aqueous solution of sodium carbonate (2M, 6.5 ml) followed by stirring at 80° C. for 6 hours. The mixture was diluted with dichloromethane and washed with water and brine. The organic layer was dried over magnesium sulfate and evaporated under reduced pressure. The residue was purified by a silica gel column chromatography eluting with 30% dichloromethane in n-hexane to give 2-methoxycarbonyl-5-(4-fluorophenyl)thiophene (1.16 g, 98.3%).

NMR (CDCl$_3$, δ): 3.86 (3H, s), 7.32 (2H, t, J=8.8 Hz), 7.59 (1H, d, J=4.0 Hz), 7.7–7.9 (3H, m) APCI-Mass m/z : 237 ($M^+$+1).

Preparation 16(2)

To a solution of 2-methoxycarbonyl-5-(4-fluorophenyl) thiophene (1.15 g) in methanol (10 ml) and tetrahydrofuran (10 ml) was added an aqueous solution of sodium hydroxide (1N, 7.3 ml) followed by stirring at 60° C. for 3 hours. To the mixture was added hydrochloric acid (1N, 8 ml). The resulting precipitate was collected by filtration and dried to give 5-(4-fluorophenyl)thiophene-2-carboxylic acid (1.06 g, 98.1%).

NMR (DMSO-$d_6$, δ): 7.30 (2H, t, J=8.8 Hz), 7.55 (1H, d, J=4.4 Hz), 7.7-7.9 (3H, m) ESI-Mass m/z: 223 ($M^+$+1).

To a suspension of 5-(4-fluorophenyl)thiophene-2 carboxcylic acid (156 mg).and 3-(1,2 dimethylimidazol-5yl)aniline (131 mg) in dichloromethane (5 ml) were added 1-ethyl-3-(3-dimethylaminopropyl)carbodiimide hydrochloride (201 mg) and 4-dimethylaminopyridine (43 mg). The mixture was stirred at ambient temperature for 72 hours and diluted with dichloromethane. The solution was washed with water and brine, dried over magnesium sulfate and evaporated under reduced pressure. The residue was purified by a silica gel column chromatography eluting with 3% methanol in dichloromethane to give N-[3-(2,3-dimethyl-3H-imidazol4-yl)-phenyl]-5-(4-fluorophenyl)thiophene-2-carboxamide (240 mg, 88.9%).

NMR (DMSO-$d_6$, δ): 2.36(3H, s), 3.56 (3H, s), 6.88 (1H, s), 7.17 (1H, d, J=7.8 Hz), 7.31 (2H, t, J=8.9 Hz), 7.44 (1H, t, J=7.9 Hz), 7.61 (1H, d, J=4.0 Hz), 7.72 (1H, d, J=8.0 Hz), 8.03 (1H, d, J=4.0Hz), 10.33 (1H, s) APCI-Mass m/z: 392 ($M^+$+1).

To a suspension of 2,3-dimethylindole-7-carboxylic acid (95 mg) and 1-hydroxybenzotriazole (81 mg) in dichloromethane (3 ml) was added 1-ethyl-3-(3-dimethylaminopropyl)carbodiimide hydrochloride (144 mg), and the mixture was stirred for 5 minutes. After adding 3-(pyrimidin-5-yl)aniline (94 mg) and 4-dimethylinopyridine (92 mg), the mixture was stirred for 24 hours. The mixture was diluted with dichloromethane and washed with water and brine. The organic layer was dried over magnesium sulfate and evaporated under reduced pressure. The residue was purified by a silica gel column chromatography eluting with 3% methanol in dichloromethane to give N-(3-(pyrimidin-5-yl)-phenyl)-2,3-dimethyl-1H-indole-7-carboxamide (117 mg, 68.4%).

NMR (DMSO-$d_6$, δ): 2.19 (3H, s), 2.37 (3H, s), 7.10 (1H, t, J=7.6 Hz), 7.5–7.7 (2H, m), 7.63 (1H, d, J=7.7 Hz), 7.77 (1H, d, J=7.7 Hz), 7.9–8.0 (1H, m), 8.30 (1H, s), 9.13 (2H, s), 9.23 (1H, s), 10.38 (1H, s), 10.81 (1H, s) APCI-Mass m/z: 343 ($M^+$+1).

EXAMPLE 18

To a suspension of 9H-carbazole-1-carboxylic acid (112 mg) and 3-(1,3,4-triazol-1-yl)aniline (147 mg) in dichloromethane (3 ml) were added 1-ethyl-3-(3-dimethylaminopropyl)carbodiimide hydrochloride (188 mg) and 4-dimethylaminopyridine (43 mg). The mixture was stirred at ambient temperature for 24 hours and diluted with dichloromethane. The solution was washed with water and brine, dried over magnesium sulfate and evaporated under reduced pressure. The residue was triturated with methanol. The resulting precipitate was collected by filtration and dried to give N-(3-([1,2,4]triazol-4-yl)phenyl)-9H-carbazole-1-carboxamide (38 mg, 15.4%).

NMR (DMSO-$d_6$, δ): 7.20 (1H, t, J=7.4 Hz), 7.33 (1H, t, J=7.7 Hz), 7.3–7.5 (2H, m), 7.60 (1H, t, J=8.0 Hz), 7.72 (1H, d, J=8.0 Hz), 7.89 (1H, d, J=8.4 Hz), 8.1–8.3 (3H, m), 8.40 (1H, d, J=7.5 Hz), 9.09 (2H, s), 10.65 (1H, s), 11.54 (1H, s) APCI-Mass m/z: 354 ($M^+$+1).

EXAMPLE 19

To a suspension of 2-trifluoromethyl-3-methylindole-7-carboxylic acid (122 mg) and 4-methyl-3-(pyrimidin-5-yl) aniline (93 mg) in dichloromethane (5 ml) were added 1-ethyl-3-(3-dimethylaminopropyl)carbodiimide hydrochloride (144 mg) and 4-dimethylaminopyridine (30 mg). The mixture was stirred at ambient temperature for 24 hours and diluted with dichloromethane. The solution was washed with water and brine, dried over magnesium sulfate and evaporated under reduced pressure. The residue was purified by a silica gel column chromatography eluting with 2% methanol in dichloromethane to give N-[4-methyl-3-(pyrimidin-5-yl)-phenyl]-3-methyl-2-trifluoromethyl-1H-indole-7-carboxamide (155 mg, 75.6%).

NMR (OMSO-$d_6$, δ): 2.28 (3H, s), 2.44 (3H, d, J=2.0 Hz), 7.29 (1H, t, J=7.7 Hz), 7.3–7.4 (1H, m), 7.8–8.0 (4H, m), 8.90 (2H, s), 9.24 (1H, s), 10.49 (1H, s), 11.44 (1H, s) APCI-Mass m/z: 411 ($M^+$+1).

EXAMPLE 20

To a suspension of 2-tifluoromethyl-3-methylidole-7-carboxylic acid (122 mg) and 3-(1,2,4-triazol-1-yl)aniline (80 mg) in dichloromethane (5 ml) were added 1-ethyl-3-(3-dimethylaminopropyl)carbodiimide hydrochloride (144 mg) and 4-dimethylaminopyridine (30 mg). The mixture was stirred at ambient temperature for 72 hours and diluted with dichloromethane. The solution was washed with water and brine, dried over magnesium sulfate and evaporated under reduced pressure. The residue was triturated with methanol. The resulting precipitate was collected by filtration and dried to give N-[3-(1,2,4triazol-1-yl)-phenyl]-3-methyl-2-trifluoromethyl-1H-indole-7-carboxamide (97 mg, 50.3%).

NMR (DMSO-$d_6$, $\delta$): 2.45 (3H, d, J=2.0 Hz), 7.31(1H, t, J=7.7 Hz), 7.5–7.7 (2H, m), 7.82 (2H, m), 8.27 (2H, s), 8.51 (1H, s), 9.29 (1H, s), 10.68 (1H, s) 11.53 (1H, s) APCI-Mass m/z: 386 ($M^+$+1).

Preparation 2(1)

A suspension of 5-bromopyrimidine(1.52 g),2-methylphenylboronic acid (1.43 g), sodium carbonate (3.04 g) and 10% palladium on charcoal (50% wet, 0.85 g) was refluxed for 24 hours. The mixture was filtered and the filtrate was concentrated under reduced pressure. To the residue ethyl acetate was added and the mixture was washed with water and brine. The separated organic layer was dried over magnesium sulfate and evaporated under pressure to give 5-(2-methylphenyl)pyrimidine (1.61 g, 98.7%).

NMR (DMSO-$d_6$, $\delta$): 2.27 (3H, s), 7.3–7.5 (4H, m), 8.87 (2H, s), 9.21 (1H, s) APCI-Mass m/z: 171 ($M^+$+1).

Preparation 21(2)

To a suspension of 5-(2-methylphenylpyrimidine (0.85 g) in concentrated sulfuric acid (10 ml) was portionwise added potassium nitrate (556 mg) at 5° C. The mixture was stirred at 5° C. for 30 minutes and poured into crushed ice. The pH of the mixture was adjusted to 8.0 with an aqueous sodium hydroxide solution (4N) and extracted with ethyl acetate. The organic layer was washed with water twice and brine, dried over magnesium sulfate and evaporated under reduced pressure.

The residue was triturated with methanol. The resulting precipitate was collected by filtration, washed with methanol and dried to give 5-(2-methyl-5-nitrophenyl)pyrimidine (662 mg,61.3%).

NMR (DMSO-$d_6$, $\delta$): 2.38 (3H, s), 7.68 (1H, d. J=8.2 Hz), 8.2–8,4 (2H, m), 8.96 (2H, s), 9.28 (1H, s) APCI-Mass m/z 216 ($M^+$+1).

Preparation 21(3)

A suspension of 5-(2-methyl-5-nitrophenyl)pyrimidine (0.431 g) in tetrahydrofuran (4 ml) and methanol (4 ml) was hydrogenated over palladium on carbon (10% w/w, 50% wet, 129 mg) under hydrogen atmosphere for 2 hours. The catalyst was filtered off, and the filtrate was evaporated under reduced pressure to give 5-(5-amino-2-methylphenyl) pyrimidine (370 mg, 99.7%).

NMR (DMSO-$_6$, $\delta$): 2.07 (3H, s), 5.05 (2H, s), 6.48 (1H, d, J=2.4 Hz), 6.58 (1H, dd, J=8.0 Hz, 2.4 Hz), 6.99 (1H, d, J=8.0 Hz), 8.78 (2H, s), 9.16 (1H, s) APCI-Mass m/z: 186 ($M^+$+1).

EXAMPLE 21

To a suspension of 4-methyl-3-(pyrimidin-5-yl)aniline (0.111 g) and pyridine (0.15 ml) in dichloromethane (2 ml) was dropwise added a solution of the fluorene-1-carbonyl chloride (0.137 g) in dichloromethane (2 ml) followed by stirring for 2 hours. The mixture was diluted with dichloromethane and washed with an aqueous solution of sodium hydrogen carbonate and brine. The separated organic layer was dried over sodium sulfate and evaporated under reduced pressure. The residue was triturated with methanol. The resulting solid was collected by filtration to give N-(4-methyl-3-(pyrimidin-5-yl)-phenyl)-9H-fluorene-1-carboxamide (0.167 g, 73.9%)

NMR (DMSO-$d_6$, $\delta$): 2.25 (3H, s), 4.20 (2H, s), 7.3–7.5 (2H, m), 7.5–7.7 (2H, m), 7.7–7.9 (2H. m), 7.97 (1H, d, J=6.5 Hz), 8.11 (1H, d, J=7.1 Hz), 8.90 (2H, s), 9.24 (1H, s), 10.41 (1H, s) APCI-Mass m/z: 378 ($M^+$+1).

EXAMPLE 22

To a suspension of 9H-carbazole-1-carboxylic acid (148 mg) and 1-hydroxybenzotriazole (130 mg) in dichloromethane (3 ml) was added 1-ethyl-3-(3-dimethylaminopropyl)carbodiimide hydrochloride (201 mg) and the mixture was stirred for 5 minutes. After adding 4-methyl-3-(pyrimidin-5-yl)aniline (130 mg) and 4-dimethylaminopyridine (128 mg), the mixture was stirred for 24 hours. The mixture was diluted with dichloromethane and washed with water and brine. The organic layer was dried over magnesium sulfate and evaporated under reduced pressure. The residue was purified by a silica gel column chromatography eluting with 2% methanol in dichloromethane to give N-(4-methyl-3-(pyrimidin-5-yl)-phenyl)-9H-carbazole-1-carboxamide (140 mg, 52.8%)

NMR (DMSO-$d_6$, $\delta$): 2.28 (3H, s), 7.20 (1H, t, J=7.4 Hz), 7.31 (1H, t, J=7.8 Hz), 7.3–7.5 (2H, m), 7.70 (1H, d, J=8.0 Hz), 7.86 (1H, d , J=8.2 Hz), 7.95 (1H, d, J=2.0 Hz), 8.15 (2H, t, J=7.4 Hz), 8.37 (1H, d, J=7.6 Hz), 8.93 (2H, s), 9.25 (1H, s), 10.47 (1H, s), 11.52 (1H, s) APCI-Mass m/z: 379 ($M^+$+1).

Preparation 23

To a suspension of 2,2'-bithiophene (1.0 g) in tetrahydrofuran (10 ml) was added a solution of n-butyl lithium in n-hexane (1.54 M, 4.3 ml) at −25° C. under nitrogen atmosphere. The mixture was stirred at −60° C. for 30 minutes. To the solution dry-ice (1.0 g) was added and the mixture was stirred at ambient temperature for 30 minutes. To the resultant suspension hydrochloric acid (1N, 10 ml) and ethyl acetate were added. The separated organic layer was washed with brine, dried over magnesium sulfate and evaporated under reduced pressure. The residue was triturated with diisopropyl ether. The resulting precipitate was collected by filtration, washed with diisopropyl ether and dried to give [2,2']bithiophenyl-5-carboxylic acid (952 mg, 75.6%).

NMR (DMSO-$d_6$, $\delta$): 7.14 (1H, t, J=4.3 Hz), 7.35 (1H, d, J=3.8 Hz), 7.4–7.8 (3H, m), 12.5–13.5 (1H, broad s) APCI-Mass m/z: 211 ($M^+$+1).

EXAMPLE 23

To a suspension of [2,2']bithiophenyl-5-carboxylic acid (105 mg) and 1-hydroxybenzotriazole (81 mg) in dichloromethane (2 ml) was added 1-ethyl-3-(3-dimethylaminopropyl)carbodiimide hydrochloride (144 mg) and the mixture was stirred for 15 minutes. After adding 3-(1,2-dimethylimidazol-5-yl)aniline (94 mg) and 4-dimethylaminopyridine (92 mg), the mixture was stirred for 24 hours. The mixture was diluted with dichloromethane and washed with water and brine. The mixture was dried over magnesium sulfate and evaporated under reduced pressure. The residue was purified by a silica gel column chromatography eluting with 3% methanol in dichloromethane to give N-[3-(2,3-dimethyl-3H-imidazol-4-yl)-phenyl]-[2,2']bithiophenyl-5-carboxamide (117 mg, 61.6%).

NMR DMSO-d$_6$, δ): 2.36(3H, s), 3.54 (3H, s), 6.88 (1H, s), 7.1–7.2 (2H, m), 7.4–7.6 (3H, m), 7.62 (1H, dd, J=5.1 Hz, 1.1 Hz), 7.7–7.9 (2H, m), 7.99 (1H, d, J=4.0 Hz), 10.33 (1H, s) APCI-Mass m/z: 380 (M$^+$+1).

EXAMPLE 24

N-(3-(Imidazol-1-yl)phenyl)-1-phenylpyrrole-3-carboxamide was prepared in a manner Far to Example 12.

mp: 100–103° C. (diisopropyl ether/ethyl acetate) IR (KBr, ν): 1645 cm$^{-1}$ NMR (DMSO-d$_6$, δ): 6.88 (1H, s), 7.13 (1H, s), 7.30–7.80 (10H, m), 8.04 (1H, s), 8.10–8.20 (2H, m), 9.89 (1H, s). Mass m/z: 329 (M$^+$+1).

To 2-phenylthiazole-4-carboxylic acid (70 mg) in 5 mL benzene was added thionyl chloride(0.075 mL) at room temperature. The mixture was heated under reflux for an hour The mixture was cooled and evaporated under reduced pressure. To the mixture added was dichloromethane (10 ml) followed by 3-(imidazol-1-yl)aniline (54 mg) and triethylamine (0.1 ml). The mixture was stirred at room temperature for an hour. The mixture was washed with a saturated aqueous sodium bicarbonate solution, dried with sodium sulfate and evaporated. The residue was recrystallized from diisopropyl ether/ethyl acetate to give N-(3-(imidazol-1-yl)phenyl)-2-phenylthiazole-4-carboxamide.

mp: 131–134° C. IR (nujol, ν): 1665 cm$^{-1}$ NMR (DMSO-d$_6$, δ): 7.14 (1H, s), 7.42 (1H, d, J=9 Hz), 7.45–7.60 (4H, m), 7.72 (1H, s), 7.94 (1H, d, J=8 Hz), 8.10–8.25 (4H, m), 8.54 (1H, s), 10.41 (1H,s) Mass m/z: 347 (M$^+$+1).

Preparation 26 (1)

To a suspension of m-nitroaniline (2.0 g), phosphoric acid (1.67 ml), butane-2,3-dione (1.27 ml) and an aqueous solution of formaldehyde (35% w/w, 1.24 ml) in water (15 ml) was added an aqueous solution of ammonium chloride (5M, 6 ml) dropwise at 100° C. After stirring for 2 hours at 100° C., the mixture was poured into an aqueous saturated sodium hydrogen carbonate solution. The mixture was extracted with ethyl acetate. The separated organic layer was washed with water and brine, dried over magnesium sulfate and evaporated under reduced pressure. The residue was purified with a silica gel column chromatography eluting with 0–3% methanol/dichloromethane to give 4,5-dimethyl-1-(3-nitrophenyl)imidazole (135 mg, 4.3%).

APCI-mass m/z: 218 (M$^+$+1) NMR (DMSO-d$_6$, δ); 2.12 (3H, s), 7.7–7.9 (3H, m), 8.23 (1H, t, J=2.1 Hz), 8.28 (1H, dd, J=1.5 Hz, 8.0 Hz).

Preparation 26 (2)

A suspension of 4,5-dimethyl-1-(3-nitrophenyl)imidazole (130 mg) in methanol (2 ml) and tetrahydrofuran (2 ml) was hydrogenated over palladium on carbon (10% w/w, 50% wet, 50 mg) under hydrogen atmosphere for 3 hours. The catalyst was filtered off, and the filtrate was evaporated under reduced pressure to give 3-(4,5-dimethyl-imidazol-1-yl)aniline (110 mg, 98.2%).

APCI-Mass 188 (M$^+$+1) NMR (DMSO-d$_6$, δ) ; 2.05 (3H, s), 2.08 (3H, s), 5.39 (2H, s), 6.43(1H, d, J=7.6 Hz), 6.48 (1H, s), 6.60 (1H, d, J=8.1 Hz), 7.12 (1H, t, J=8.0 Hz), 7.52 (1H, s).

Preparation 26 (3)

To a suspension of N-formyl-3-nitroaniline (831 mg) and potassium carbonate (830 mg) in N,N-dimethylformamide (5 ml) was added 2-bromo-3-butanone (906 mg), and the mixture was stirred for 72 hours. The mixture was diluted with ethyl acetate and washed with water and brine. The mixture was dried over magnesium sulfate and evaporated to give N-(1-methyl-2-oxo-propyl)-N-(3-nitrophenyl)formamide (1.18 g, 100%).

APCI-Mass m/z :237 (M$^+$+1) NMR (DMSO-d$_6$, δ); 1.35 (3H, d, J=7.1 Hz), 2.18 (3H, s), 4.79 (1H, q, J=7.1 Hz);,7.74 (1H, t, J=8.2 Hz), 7.83 (1H, d, J=8.2 Hz), 8.1–8.2 (2H, m), 8.48 (1H, s)

Preparation 26 (4)

A suspension of N-(1-methyl-2-oxo-propyl)-N-(3-nitrophenyl)formamide (1.17 g), ammonium acetate (3.82 g) and acetic acid (1 ml) in xylene (20 ml) was refluxed for 2 hours. After adding ethyl acetate and an aqueous solution of sodium hydroxide (1N, 100 ml), the mixture was stirred for 10 minutes. The separated aqueous layer was extracted with ethyl acetate. The combined organic layers were washed with water and brine, dried over magnesium sulfate and evaporated under reduced pressure. The residue was purified with a silica gel column chromatography eluting with 1–3% unethanol/dichloromethane to give 4,5-dimethyl-1-(3-nitrophenyl)imidazole (0.79 g, 73.1%).

APCI-Mass m/z :218 (M$^+$+1) NMR (DMSO-d$_6$) δ; 2.13 (6H, s), 7.7–8.0 (3H, m), 8.23 (1H, t, J=2.1 Hz), 8.28 (1H, dd, J=1.5 Hz, 8.0 Hz).

EXAMPLE 26

To a suspension of 9H-carbazole-1-carboxylic acid (116 mg) and 3-(4,5dimethylimidazol-1-yl)aniline (103 mg) in dichloromethane (5 ml) were added 1-ethyl-3-(3-dimethylaminopropyl)carbodiimide hydrochloride (158 mg) and 4-dimethylaminopyridine (101 mg), and the mixture was stirred for 20 hours. The mixture was diluted with dichloromethane and washed with water and brine. The mixture was dried over magnesium sulfate and evaporated under reduced pressure. After trituration with methanol, the residue was collected by filtration and dried to give N-[3-(4,5-dimethylimidazol-1-yl)-phenyl]-9H-carbazole-1-carboxamide (86 mg, 41.1%.

APCI-mass m/z: 381 (M$^+$+1) NMR (DMSO-d$_6$) δ; 2.14 (6H, s), 7.1–7.3 (2H, m), 7.32 (1H, t, J=7.6 Hz), 7.42 (1H, t, J=7.3 HZ), 7.55 (1H, t, J=8.0 Hz), 7.66 (1H, s), 7.70 (1H, d, J=8.0 Hz), 7.92 (1H, d, J=8.0 Hz), 8.00 (1H, s), 8.12 (1H, d, J=7.6 Hz), 8.18 (1H, d, J=7.6 Hz), 8.40 (1H, d, J=7.6 Hz), 10.60 (1H, s), 11.50 (1H, s).

Preparation 27(1)

To a suspension of N-formyl-3-nitroaniline (1.0 g) in N,N-dimethylformamide (10 ml) was added sodium hydride (60% dispersion in mineral oil, 264 mg), and the mixture was stirred for 20 minutes under nitrogen atmosphere. After a solution of 1-chloropropan-2-one (0.573 ml) in N,N-dimethylformamide (5 ml) was added dropwise to the mixture, the mixture was stirred for 2 hours and diluted with ethyl acetate and water. The separated organic layer was washed with brine, dried over magnesium sulfate and evaporated under reduced pressure. The residue was purified with a silica gel column chromatography eluting with 2% methanol in dichloromethane to give N-(3-nitrophenyl)-N-(2-oxopropyl)-formamide (280 mg, 21.0%).

APCI-Mass m/z : 223 (M$^+$+1) NMR (DMSO-d$_6$, δ) ; 2.19 (3H, s), 4.78 (2H, s), 7.6–7.8 (2H, m), 8.1–8.2 (2H, m), 8.73 (1H,s).

Preparation 27 (2)

A suspension of N-(3-nitrophenyl)-N-(2-oxo-propyl)-formamide (265 mg), ammonium acetate (919 mg) and acetic acid (0.3 ml) in xylene (5 ml) was refluxed for 2.5 hours and then evaporated under reduced pressure. To the residue were added ethyl acetate and an aqueous solution of sodium hydroxide (1N, 25 ml), and the mixture was stirred for 10 minutes. The separated organic layer was washed with water and brine, dried over magnesium sulfate and evaporated to give 4-methyl-1-(3-nitrophenyl)imidazole (203 mg, 83.9%).

APCI-Mass m/z :204 (M⁺+1) NMR (DMSO-$d_6$, δ); 2.17 (3H, s), 7.65 (1H, s), 7.78 (1H, t, J=8.2 Hz), 8.1–8.2 (2H, m), 8.36 (1H, d, J=3.1 Hz), 8.44 (1H, t, J=2.2 Hz).

Preparation 27 (3)

A suspension of 4-methyl-1-(3-nitrophenyl)imidazole (198 mg) in methanol (2 ml) was hydrogenated over palladium on carbon (10% w/w, 50% wet, 100 mg) under hydrogen atmosphere for 2 hours. After the catalyst was filtered off, the filtrate was evaporated under reduced pressure to give 3-(4-methyl-imidazolyl)aniline (162 mg, 95.9%).

APCI-Mass m/z: 174 (M⁺+1) NMR (DMSO-$d_6$, δ); 2.14 (3H, s), 5.35 (2H, s), 6.51 (1H, d, J=7.0 Hz), 6.6–6.8 (2H, m), 7.09 (1H, t, J=7.8 Hz), 7.23 (1H, s), 7.91 (1H, d, J=1.2 Hz).

EXAMPLE 27

To a suspension of 9H-fluorene-1-carboxylic acid (79 mg) and 3-(4-methylimidazol-1-yl)aniline (65 mg) in dichloromethane (2 ml) was added 1-ethyl-3-(3-dimethylaminopropyl)carbodiimide hydrochloride (101 mg) and 4-dimethylaminopyridine (23 mg), and the mire was stirred for 24 hours. The mix e was diluted with dichloromethane, washed with water and brine. The mixture was dried over magnesium sulfate and evaporated under reduced pressure. The residue was triturated with methanol, and the insoluble material was collected by filtration and dried to give N-[3-(4-methylimidazol-1-yl)-phenyl]-9H-fluorene-1-carboxamide (40 mg, 29.2%).

APCI-mass m/z: 366 (M⁺+1) NMR (DMSO-$d_6$) δ; 2.18 (3H, s), 4.21 (2H, s), 7.3–7.8 (9H, m), 7.98 (1H, d, J=6.5 Hz), 8.0–8.1 (2H, m), 8.13 (1H, d, J=7.3 Hz), 10.53 (1H, s).

EXAMPLE 28

To a suspension of 9H-fluorene-1-carboxylic acid (106 mg) and 3-(4,5-dimethylimidazol-1-yl)aniline (94 mg) in dichloromethane (2 ml) were added 1-ethyl-3-(3-dimethylaminopropyl)carbodiimide hydrochloride (135 mg) and 4-dimethylaminopyridine (31 mg), and the mixture was stirred for 24 hours. The mixture was diluted with dichloromethane and washed with water and brine. The mixture was dried over magnesium sulfate and evaporated under reduced pressure. The residue was triturated with methanol, and the insoluble material was collected by filtration and dried to give N-[3-(4,5-dimethylimidazol-1-yl)-phenyl]-9H-fluorene-1-carboxamide (123 mg, 64.7%).

APCI-mass m/z: 380 (M⁺+1) NMR (DMSO-$d_6$, δ); 2.13 (6H, s), 4.20 (2H, s), 7.15 (1H, d, J=8.4 Hz), 7.3–7.5 (6H, m), 7.75 (1H, d, J=6.9 Hz), 7.8–7.9 (2H, m), 7.98 (1H, d, J=6.6 Hz), 8.13 (1H, d, J=6.9 Hz), 10.57 (1H, s):

EXAMPLE 29

To a suspension of 3-(2-thienyl)benzoic acid (103 mg) and 3-(4,5-dimethylimidazol-1-yl)aniline (94 mg) in dichloromethane (2 ml) were added 1-ethyl-3-(3-dimethylaminopropyl)carbodiimide hydrochloride (135 mg) and 4-dimethylaminopyridine (31 mg), and the mixture was stirred for 24 hours. The mixture was diluted with dichloromethane and washed with water and brine. The mixture was dried over magnesium sulfate and evaporated under reduced pressure. The residue was triturated with methanol, and the insoluble material was collected by filtration and dried to give N-[3-(4,5-dimethylimidazol-1-yl)-phenyl]-3-(2-thienyl)benzamide (117 mg, 62.6%).

APCI-mass m/z: 374 (M⁺+1) NMR DMSO-$d_6$, δ) ; 2.12 (6H, s), 7.1–7.3 (2H, m), 7.52 (1H, t, J=8.0 Hz), 7.6–7.8 (4H, m), 7.8–8.0 (4H, m), 8.18 (1H, s), 10.57 (1H, s).

Preparation 30 (1)

To a solution of N-(4fluorophenyl)-2,2-dimethylpropionamide (195 mg) in tetrahydrofuran (2 ml) was added a solution of n-butyl lithium in n-hexane (1.54M, 1.5 ml) dropwise at 0° C. under nitrogen atmosphere, and the mixture was stirred for 2 hours at 0° C. To the reaction mixture was added triisopropyl borate (0.692 ml) at −40° C., and the mixture was stirred for 30 minutes at ambient temperature. To the mixture was added 1N-hydrochloric acid (3 ml), and the mixture was diluted with ethyl acetate and water. The separated organic layer was washed with brine, dried over magnesium sulfate and evaporated under reduced pressure. To the residue were added methyl 3-bromo-2-fluorobenzoate (117 mg), tetrakis (triphenylphosphine)palladium (29 mg), an aqueous solution of sodium carbonate (2M, 2 ml) and 1,2-dimethoxyethane (5 ml). The resulting mixture was stirred under nitrogen atmosphere for 48 hours at 75° C., and diluted with ethyl acetate and water. The separated organic layer was washed with brine, dried over magnesium sulfate and evaporated under reduced pressure. The residue was purified with a silica gel column chromatography eluting with 20% ethyl acetate/n-hexane to give 2'-(2,2-dimethylpropionamido)-2,5'-difluoro-biphenyl-3-carboxylic acid methyl ester (106 mg, 60.9%).

APCI-mass m/z: 348 (M⁺+1) NMR (DMSO-$d_6$, δ); 0.96 (9H, s), 3.85 (3H, s), 7.2–7.4 (4H, m), 7.52 (1H, dt, J=2.0 Hz, 7.1 Hz), 7.86 (1H, dt, J=1.9 Hz, 7.3 Hz), 8.92 (1H, s).

Preparation 30 (2)

A mixture of 2'-(2,2-dimethyl-propionamido)-2,5'-difluoro-biphenyl-3-carboxylic acid methyl ester (92 mg) and pyridinium chloride (3.0 g) was stirred for 3 hours at 200° C., and then poured into ice-water. The suspension was stirred for 10 minutes. The precipitate was collected by filtration, washed with water and dried to give 6-fluoro-9H-carbazole-1-carboxylic acid (46 mg, 76.7%).

ESl-mass m/z: 228 (M⁺+1) NMR (DMSO-$d_6$, δ) ; 7.2–7.4 (2H, m), 7.73 (1H, dd, J=4.6 Hz, 8.9 Hz), 8.0–8.1 (2H, m), 8.42 (1H, d, J=7.3 Hz), 11.38 (1H, s), 13.19 (1H, broad s).

Preparation 30 (3)

A suspension of 3-bromonitrobenzene (20.2 g), 1,2-dimethyl-1H-imidazole (19.2 g), palladium acetate (1.12 g) and potassium carbonate (27.6 g) in N,N-dimethylformamide (500 ml) was stirred under nitrogen atmosphere for 24 hours at 140° C., and evaporated under reduced pressure. The residue was diluted with ethyl acetate and washed with water three times. The separated organic layer was washed with brine, dried over magnesium sulfate and evaporated under reduced pressure to give 3-(1,2-dimethyl-imidazol-1-yl)nitrobenzene (19.2 g).

APCI-Mass m/z: 218 (M⁺+1) NMR (DMSO-$d_6$, δ) ; 2.37(3H, s), 3.58 (3H, s), 7.09 (1H, s), 7.74 (1H, t, J=7.9 Hz), 7.91 (1H, d, J=7.7 Hz), 8.1–8.3 (2H, m).

Preparation 30 (4)

A suspension of 3-(1,2-dimethyl-1H-imidazol-5-yl) nitrobenzene (19.2 g) in methanol (200 ml) was hydrogenated over palladium on carbon (10% w/w, 50% wet, 5 g) under hydrogen atmosphere for 10 hours. After the catalyst was filtered off, the filtrate was evaporated under reduced pressure. The residue was triturated with ethyl acetate and diisopropyl ether to give 3-(1,2-dimethyl-imidazol-5-yl) aniline (14.65 g).

APCI-Mass m/z: 188 (M⁺+1) NMR (DMSO-$d_6$, δ); 2.32 (3H, s), 3.49 (3H, s), 5.16 (2H, s), 6.5–6.7 (3H, m), 6.73 (1H, s), 7.07 (1H, t, J=7.7 Hz).

EXAMPLE 30

To a suspension of 6-fluoro-9H-carbazole-1-carboxylic acid (37 mg) and 3-(1,2-dimethylimidazol-5-yl)aniline (43 mg) in dichloromethane (1 ml) were added 1-ethyl-3-(3-dimethylaminopropyl)carbodiimide hydrochloride (53 mg) and 4-dimethylaminopyridine (11 mg), and the mixture was stirred for 40 hours. The mixture was diluted with dichloromethane and washed with water and brine. The mixture was dried over magnesium sulfate and evaporated under reduced pressure. The residue was purified with a silica gel column chromatography eluting with 2–3% methanol/dichloromethane to give N-[3-(1,2-dimethylimidazol-5-yl)-phenyl]-6-fluoro-9H-carbazole-1-carboxamide (38 mg, 51.4%).

APCI-mass m/z: 399 ($M^+$+1) NMR (DMSO-$d_6$, δ) ; 2.37(3H, s), 3.59 (3H, s), 6.90 (1H, s), 7.2–7.4 (3H, m), 7.47 (1H, t, J=7.9 Hz), 7.70 (1H, dd, J=4.6 Hz, 8.9 Hz), 7.88 (1H, d, J=8.1 Hz), 7.95 (1H, s), 8.03 (1H, d, J=2.5 Hz, 9.4 Hz), 8.14 (1H, d, J=7.2 Hz), 8.40 (1H, d, J=7.6 Hz), 10.48 (1H, s), 11.55 (1H, s).

Preparation 31 (1)

To a suspension of 2-hydrazinobenzoic acid hydrochloride (2.0 g) in acetic acid (8 ml) was added dropwise a solution of 2-butanone (0.9 ml) in acetic acid (2 ml), and the resultant mixture was heated at 80° C. for one hour. After 6N-hydrochloric acid (8 ml) was added to the reaction mixture, the mixture was heated at 100° C. for 5 hours. The mixture was diluted with water (18 ml), and allowed to cool to 40° C. The resultant precipitate was collected by filtration, washed with a small amount of diisopropyl ether and dried in vacuo to give 2,3-dimethyl-1H-indole-7-carboxylic acid (0.78 g).

APCI-mass m/z: 190 ($M^+$+1) NMR (DMSO-$d_6$, δ); 2.17 (3H, s), 2.36 (3H, s), 7.02 (1H, t, d=7.6 Hz), 7.63 (2H, d, d=7.6 Hz), 10.55 (1H, brs), 12.82 (1H, brs).

EXAMPLE 31

To a suspension of 2,3-dimethyl-1H-indole-7-carboxylic acid (95 mg) and 3-(4,5-dimethylimidazol-1-yl)aniline (94 mg) in dichloromethane (2 ml) were added 1-ethyl-3-(3-dimethylaminopropyl)carbodiimide hydrochloride (135 mg) and 4-dimethylaminopyridine (31 mg), and the mixture was stirred for 12 hours. The mixture was diluted with dichloromethane and washed with water and brine. The mixture was dried over magnesium sulfate and evaporated under reduced pressure. The residue was triturated with dichloromethane, and the insoluble material was collected by filtration and dried to give N-[3-(4,5-dimethyl-imidazol-1-yl)-phenyl]-2,3-dimethyl-1H-indole-7-carboxamide (77 mg, 43.0%).

APCI-mass m/z: 359 ($M^+$+1) NMR (DMSO-$d_6$, δ); 2.12 (6H, s), 2.19 (3H, s), 2.36 (3H, s), 7.07 (1H, d, J=7.6 Hz), 7.1–7.2 (1H, m), 7.51 (1H, t, J=8.0 Hz), 7.62 (1H, d, J=7.6 Hz), 7.64 (1H, s), 7.72 (1H, d, J=7.4 Hz), 7.88 (1H, d, J=8.0 Hz), 7.96 (1H, t, J=2.0 Hz), 10.42 (1H, s), 10.77 (1H, s).

EXAMPLE 32

To a suspension of 6-fluoro-9H-carbazole-1-carboxylic acid (70 mg) and 3-(4,5-dimethylimidazol-1-yl)aniline (60 mg) in dichloromethane (2 ml) were added 1-ethyl-3-(3-dimethylaminopropyl)carbodiimide hydrochloride (88 mg) and 4-dimethylaminopyridine (19 mg), and the mixture was stirred for 40 hours. The mixture was diluted with dichloromethane and washed with water and brine. The mixture was dried over magnesium sulfate and evaporated under reduced pressure. The residue was purified with a silica gel column chromatography eluting with 2–3% methanol/dichloromethane to give N-[3-(4,5-diethylimidazol-1-yl)-phenyl]-6-fluoro-9H-carbazole-1-carboxamide (65 mg, 53.7%).

APCI-mass m/z: 399 ($M^+$+1) NMR (DMSO-$d_6$, δ); 2.14 (6H, s), 7.17 (1H, d, J=7.9 Hz), 7.3–7.5 (2H, m), 7.55 (1H, t, J=8.0 Hz), 7.6–7.8 (2H, m), 7.92 (1H, d, J=8.3 Hz), 8.0–8.1 (2H, m), 8.14 (1H, d, J=7.1 Hz), 8.41 (1H, d, J=7.5 Hz), 10.60 (1H, s), 11.56 (1H, s).

EXAMPLE 33

To a suspension of 9H-carbazole-1-carboxylic acid (106 mg) and 3-(4-methylimidazol-1-yl)aniline (87 mg) in dichloromethane (5 ml) were added 1-ethyl-3-(3-dimethylaminopropyl)carbodiimide hydrochloride (144 mg) and 4-dimethylaminopyridine (31 mg), and the mixture was stirred for 40 hours. The mixture was diluted with dichloromethane and washed with water and brine. The mixture was dried over magnesium sulfate and evaporated under reduced pressure. The residue was triturated with methanol, and the insoluble material was collected by filtration and dried to give N-[3-(4-methylimidazol-1-yl)-phenyl]-9H-carbazole-1-carboxamide (68 mg, 37.0%).

APCI-mass m/z: 367($m^+$+1) NMR (DMSO-$b_6$, δ); 2.19 (3H, s), 7.20 (1H, t, J=7.5 Hz), 7.3–7.5 (4H, m), 7.52 (1H, t, J=8.0 Hz), 7.72 (1H, d, J=8.0 Hz), 7.80 (1H, d, J=8.4 Hz), 8.09 (1H, d, J=9.2 Hz), 8.2–8.3 (3H, m), 8.40 (1H, d, J=7.6 Hz), 10.56 (1H, s), 11.53 (1H, s).

What is claimed is:

1. A compound of formula (I):

$$R^2 \underset{}{\overset{R^1}{\underset{}{\bigodot}}} NHCO-R^3 \quad (I)$$

wherein $R^1$ is a 4-(lower) alkyl-imidazol-1-yl or a 4,5-di(lower) alkyl-imidazol-1-yl group, $R^2$ is a hydrogen atom or a lower alkyl group, and $R^3$ is a fluorenyl group, or pharmaceutically acceptable salts thereof.

2. A pharmaceutical composition, which has 5-HT antagonism activity, comprising a compound of claim 1 or its non-toxic pharmaceutically acceptable salt together with pharmaceutical carrier.

3. The compound of formula (I) of claim 1, wherein the compound is in the form of a pharmaceutically acceptable salt.

4. The compound of formula (I) of claim 3, wherein the compound is in the form of a salt of an inorganic base, a salt of an organic base, an inorganic addition salt, an organic carboxylic or sulfonic salt, a salt of a basic or acidic amino acid, or mixtures thereof.

5. The compound of formula (l) of claim 4, wherein the compound is in the form of a salt of an alkali metal or a salt of an alkaline earth metal.

6. The compound of formula (I) of claim 4, wherein the compound is in the form of a triethylamine salt, a pyridine salt, a picoline salt, an ethanolamine salt, a triethanolamine salt, a dicyclohexylamine salt, or an N,N'-dibenzylethylenediamine salt.

7. The compound of formula (I) of claim 4, wherein the compound is in the form of a hydrochloride salt, a hydrobromide salt, a hydriodide salt, a sulfate salt, or a phosphate salt.

8. The compound of formula (I) of claim 4, wherein the compound is in the form of a formate salt, an acetate salt, a trifluoroacetate salt, a maleate salt, a tartrate salt, a methanesulfonate salt, a benzenesulfonate salt, or a p-toluenesulfonate salt.

9. The compound of formula (I) of claim 7, wherein the compound is in the form of an arginine salt, a aspartate salt, or a glutamate salt.

10. The compound of formula (I) of claim 1, wherein $R^1$ is a lower alkyl group having 1 to 6 carbon atoms.

11. The compound of formula (I) of claim 1, wherein $R^1$ is a lower alkyl group having 1 to 4 carbon atoms.

12. The compound of formula (I) of claim 1, wherein $R^1$ is a lower alkyl group selected from the group consisting of methyl, ethyl, propyl, isopropyl, butyl, t-butyl, pentyl and hexyl.

13. The pharmaceutical composition of claim 2, wherein the pharmaceutical composition is in the form of a tablet, granule, powder, capsule, solution, suspension, syrup, emulsion or lemonade.

14. The pharmaceutical composition of claim 2, wherein the amount of the compound of formula (I) is 0.05 to 100 mg.

* * * * *

UNITED STATES PATENT AND TRADEMARK OFFICE
CERTIFICATE OF CORRECTION

PATENT NO. : 6,770,667 B1
DATED : August 3, 2004
INVENTOR(S) : Ito et al.

It is certified that error appears in the above-identified patent and that said Letters Patent is hereby corrected as shown below:

Title page,
Item [30], Foreign Application Priority Data, should read as follows:
-- [30]   Foreign Application Priority Data
Oct. 1, 1999     (AU)………………………..PQ3198 --

Signed and Sealed this

Seventh Day of December, 2004

JON W. DUDAS
*Director of the United States Patent and Trademark Office*